United States Patent [19]
Irick, Jr. et al.
[11] 4,281,129
[45] * Jul. 28, 1981

[54] PIPERIDINYL HYDROGEN 2-HYDROXYALKYL PHOSPHATES AND METAL SALTS THEREOF

[75] Inventors: Gether Irick, Jr.; Richard H. S. Wang, both of Kingsport, Tenn.

[73] Assignee: Eastman Kodak Company, Rochester, N.Y.

[ * ] Notice: The portion of the term of this patent subsequent to Mar. 25, 1997, has been disclaimed.

[21] Appl. No.: 81,231

[22] Filed: Oct. 2, 1979

Related U.S. Application Data

[62] Division of Ser. No. 963,716, Nov. 27, 1978, Pat. No. 4,194,989.

[51] Int. Cl.$^3$ .................... C07D 211/46; C07D 211/94
[52] U.S. Cl. .......................................... 546/6; 546/16; 546/25
[58] Field of Search ................................ 546/6, 16, 25

[56] References Cited

U.S. PATENT DOCUMENTS 4,141,883 2/1979 Soma et al. ............................ 546/25

*Primary Examiner*—Henry R. Jiles
*Assistant Examiner*—Bernard Dentz
*Attorney, Agent, or Firm*—Clyde L. Tootle; Daniel B. Reece, III

[57] ABSTRACT

The invention relates to piperidinyl hydrogen 2-hydroxyalkyl phosphates which have been found to be effective ultraviolet stabilizers. The invention also relates to piperidinyl hydrogen 2-hydroxyalkyl phosphate salts which have been found to be effective ultraviolet stabilizers. The invention also relates to ultraviolet degradable organic compositions containing a stabilizing amount of the piperidinyl hydrogen 2-hydroxyalkyl phosphates or salts thereof to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, or coated on the exterior of the molded article, film or extruded fiber.

12 Claims, No Drawings

PIPERIDINYL HYDROGEN 2-HYDROXYALKYL PHOSPHATES AND METAL SALTS THEREOF

This is a division of application Ser. No. 963,716, filed Nov. 27, 1978, now U.S. Pat. No. 4,194,989.

This invention relates to piperidinyl hydrogen 2-hydroxyalkyl phosphates or salts thereof useful as ultraviolet stabilizers and their use in organic compositions. More particularly, the invention relates to piperidinyl hydrogen 2-hydroxyalkyl phosphates or salts thereof and the stabilization of ultraviolet degradable organic compositions against deterioration resulting from the exposure to such radiations with such piperidinyl phosphates or salts thereof.

The degradative effects of ultraviolet light on various organic compositions is well known in the art. The photodeterioration or degradation is of particular concern with organic photo-degradable compositions which are exposed to ultraviolet light, such as sunlight, for long periods of time. One group of such photodegradable organic compositions are polymeric compositions such as polyolefins, polyesters, polyurethanes and the like. On exposure to sunlight for extended periods of time, these polymeric compositions degrade and their physical properties are reduced thereby rendering such polymeric compositions less useful or useless for most applications. Therefore, considerable effort has been directed to providing a solution to the photodegradation problem of polymeric compositions. As a result of this effort, there have been discovered many additives and stabilizers which improve the stability of polymeric compositions.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing piperidinyl hydrogen 2-hydroxyalkyl phosphate compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by ultraviolet radiations, including short wavelength visible radiations.

Further objects and advantages of the invention will be apparent to those skilled in the art from the accompanying disclosure and claims.

In accordance with the present invention, piperidinyl hydrogen 2-hydroxyalkyl phosphate compositions are provided which are useful as ultraviolet stabilizers. These organic compositions contain at least one piperidinyl group containing composition connected through a 2-hydroxyalkyl hydrogen phosphate moiety. The piperidinyl hydrogen 2-hydroxyalkyl phosphate compositions of the present invention have the following structures:

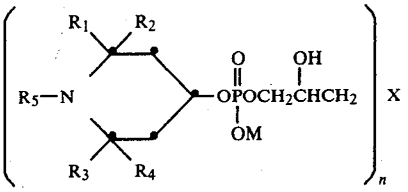

wherein $R_1$ and $R_2$ are each alkyl having 1–6 carbons; $R_3$ and $R_4$ are each alkyl having 1–6 carbons or together with the carbon to which they are bound form a cyclopentyl or cyclohexyl ring which is unsubstituted or substituted with a methyl group; $R_5$ is hydrogen, oxy, alkyl having 1 to 12 carbon atoms, β-methoxyethyl, alkenyl having 3 or 4 carbon atoms, propargyl, benzyl or alkyl substituted benzyl; and M is either hydrogen or a metal ion selected from the group consisting of Li, Na, K, Mg, Ca, Ba, Mn, Co, Ni, Sn, Zn, Ce, and the amount of hydrogen for M can vary from zero to 100%. Preferably, the amount of M is from 67 to 100 mole percent hydrogen. Since the valence of M for these metals is not always one, it is understood that the valency requirements of M may be filled by a suitable anion such as acetoxy, benzoyloxy, chloro and the like. X is an alkyl, alkylene, oxyalkyl or oxyalkyleneoxy wherein the alkyl or alkylene has 2 to 12 carbon atoms or an aryl, arylene, oxyaryl or oxyaryleneoxy with 6, 12 or 18 carbon atoms such as benzene, naphthylene and the like and which alkyl, alkylene, aryl or arylene can be substituted or unsubstituted; and n is 1 to 4.

Suitable piperidinyl groups are 2,2,6,6-tetramethylpiperidin-4-yl, 1,2,2,6,6-pentamethylpiperidin-4-yl, 1-oxo-2,2,6,6-tetramethylpiperidin-4-yl and the like.

The piperidinyl hydrogen 2-hydroxyalkyl phosphate was prepared by reacting phosphorus oxychloride with 2,2,6,6-tetramethyl-4-piperidinol to form 2,2,6,6-tetramethyl-4-piperidinyl dihydrogen phosphate, which was subsequently reacted with an epoxy compound to produce 2,2,6,6-tetramethyl-4-piperidinyl hydrogen 2-hydroxyalkyl phosphate.

The piperidinyl hydrogen 2-hydroxyalkyl phosphate compositions can be added to organic compositions which are susceptible to ultraviolet degradation. Such compositions include, for example, polymeric compositions such as polyolefins such as, for example, high, medium and low density polyethylene, polypropylene, polybutene and the like; polyamides such as N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The piperidinyl hydrogen 2-hydroxyalkyl phosphate compositions, as effective ultraviolet stabilizers, are generally used in an amount of from 0.01% to 10%, by weight, based on the weight of the organic material to which they are added. While a detectable amount of ultraviolet stabilization may be obtained with amounts less than 0.01%, this amount of stabilization would be of little practical utility in a commercial application. Moreover, while amounts greater than 10%, by weight, provide effective ultraviolet stability, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 0.5% by weight, of the stabilizer effectively stabilizes $TiO_2$-pigmented polypropylene plastic compositions.

The ultraviolet stabilized organic compositions of the present invention may also contain other additives, pigments, ultraviolet stabilizers, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel piperidinyl hydrogen 2-hydroxyalkyl phosphate ultraviolet stabilizers may be incorporated into organic compositions by melt-blending, by dissolving in a common solvent, by emulsification, or may be added onto the surface of an organic plastic material prior to being molded or extruded into a suitable object. These materials can also be added to coatings and the like which can be applied to the surface of a molded object. One of the novel features of the present piperidinyl hydrogen 2-hydroxyalkyl phosphate ultraviolet stabilizers is that the pH of the compositions is controllable. For example, the preparation of a salt or partial salt of the compositions changes the pH of the compositions. This can be important, for example, with an emulsifiable polymer that requires a base medium. The addition of an acid stabilizer could break up the emulsion and be detrimental. Therefore, the acidity of the stabilizer can be changed by formation of a salt. Also, the solubility of the compositions in organic solvents and aqueous mediums can be modified by converting the acid to a salt, for example.

This invention will be further illustrated by the following examples although it will be understood that these examples are included merely for purposes of illustration and are not intended to limit the scope of the invention.

EXAMPLE 1

1,3-Bis[3-(2,2,6,6-tetramethyl-4-piperidinyl hydrogen phosphoro)2-hydroxypropyloxy]2,2-di-methylpropane, (I) was prepared as follows:

A mixture of 2,2,6,6-tetramethyl-4-piperidinol (15.7 g., 0.10 mole) and phosphorus oxychloride (77 g, 0.5 mole) was heated at 80° C. for 4 hours. After removal of excess phosphorus oxychloride in vacuo, 40 ml of 10% sodium hydroxide solution was added and the mixture was heated at 40° C. for 6 hours. After removal of water the "product A", 2,2,6,6-tetramethyl-4-piperidinyl dihydrogen phosphate, was obtained.

Neopentylglycol diglycidyl ether (10.8 g, 0.05 mole) was added to "product A" (27.4 g, 0.10 mole) slowly with stirring at $<80°$ C. After the mixture was heated at 80° C. for 4 hours, the product I was formed.

EXAMPLE 2

The procedure for the preparation of 4,4'-bis[3-(2,2,6,6-tetramethyl-4-piperidinyl hydrogen phosphoro)2-hydroxypropyloxy]-isopropylidene dibenzene, (II) was the same as described for I except that bisphenol A diglycidyl ether was used in replacing neopentyl glycol diglycidyl ether.

EXAMPLE 3

The zinc salt of I (III) was prepared from a mixture of I (7.63 g.) and zinc acetate (1.83 g.) which was refluxed in 100 ml. of dichloromethane for 4 hours. The product III was obtained after removing the solvent by evaporation.

EXAMPLE 4

The zinc salt of II (IV) was prepared by the reaction of II (8.87 g) and zinc acetate (1.83 g) in the same manner as described in Example 3 for product (III).

The ultraviolet stabilization provided by the piperidinyl phosphates of the present invention is shown in $TiO_2$-pigmented polypropylene in Table 1.

TABLE 1

Effectiveness of Ultraviolet Stabilizers in $TiO_2$-Pigmented Polypropylene Film Exposed In Uvatest Weathering Device[1]

| Compound (0.5%) | Time to Embrittlement[4] (Hours) |
|---|---|
| none | 300 |
| I | 3500 |
| II | 3500 |
| III | 3100 |
| IV | 3100 |
| I + 0.5% Tinuvin 328[2] | 3800 |
| I + 0.5% Ferro AM-340[3] | 4000 |

[1]Ultraviolet weathering device with fluorescent lamps (310–366 nm) manufactured by Geopar Ind., Ludlow, Mass.
[2]2-(2H-Benzotriazol-2-yl)-4,6-di-tert-pentylphenol.
[3]2,4-Di-t-butylphenyl-3,5-di-t-butyl-4-hydroxybenzoate.
[4]Enbrittlement was determined by bending the films 180°around a ⅛" mandrel

TABLE 2

Effectiveness of Ultraviolet Stabilizers in Polyurethane Coating on Steel Panels[5] After QUV Cyclic Environmental Tester Exposure[6]

| Compound (1%) | % Gloss[7] Retained After 500 Hrs. Exposure |
|---|---|
| None | 12 |
| I | 78 |
| II | 80 |
| III | 68 |
| IV | 72 |
| I + 1% Tinuvin 328 | 90 |
| I + 1% Ferro AM-340 | 85 |

[5]Compositions based on QR-568 acrylic (Rohm and Haas) and Desmodur N-75 Isocyanate (Mobay) were spray applied to 4" × 12" Bonderite 40 treated steel panels primed with Inmont P41 primer (325° F. × 45 minutes).
[6]QUV Tester was manufactured by the Q-Panel Company, Cleveland, Ohio. Test conditions: 140° F., 16 hours light (FS40 flourescent sun lamps) and 110° F., 8 hours dark.
[7]Gardner Multi-Angle glossmeter, Gardner Laboratory Inc., Bethesda, Maryland.

These piperidinyl hydrogen 2-hydroxyalkyl phosphate compositions find particular utility as ultraviolet stabilizers in organic compositions requiring ultraviolet stability. Such compositions include polymeric compositions such as, for example, polyurethanes, poly-α-olefins, polyamides, acrylics, cellulose esters and the like as well as molded or shaped articles, film, and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. A piperidinyl phosphate having the formula:

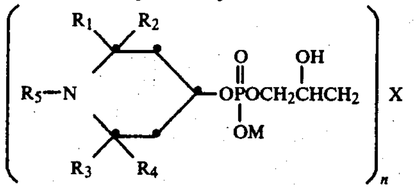

wherein $R_1$ and $R_2$ are each alkyl having 1–6 carbons; $R_3$ and $R_4$ are each alkyl having 1–6 carbons or together with the carbon to which they are bound form a cyclopentyl or cyclohexyl ring which is unsubstituted or substituted with a methyl group; $R_5$ is hydrogen, oxy, alkyl having 1 to 12 carbon atoms, β-methoxyethyl, alkenyl having 3 or 4 carbon atoms, propargyl, benzyl or alkyl substituted benzyl; M is either hydrogen or a metal ion selected from the group consisting of Li, Na, K, Mg, Ca, Ba, Mn, Co, Ni, Sn, Zn, Ce; X is an alkyl, alkylene, oxyalkyl or oxyalkyleneoxy having 2 to 12 carbon atoms or an aryl, arylene, oxyaryl or oxyaryleneoxy with 6, 12 or 18 carbon atoms; and n is 1 to 4.

2. A piperidinyl phosphate according to claim 1 having the formula:

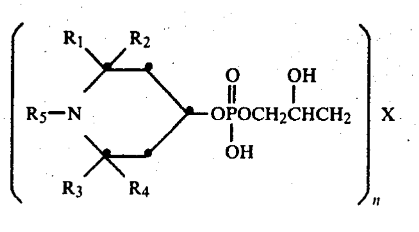

wherein $R_1$ and $R_2$ are each alkyl having 1–6 carbons; $R_3$ and $R_4$ are each alkyl having 1–6 carbons or together with the carbon to which they are bound form a cyclopentyl or cyclohexyl ring which is unsubstituted or substituted with a methyl group; $R_5$ is hydrogen, oxy, alkyl having 1 to 12 carbon atoms, β-methoxyethyl, alkenyl having 3 or 4 carbon atoms, propargyl, benzyl or alkyl substituted benzyl; X is an alkyl, alkylene, oxyalkyl or oxyalkyleneoxy having 2 to 12 carbon atoms or an aryl arylene, oxyaryl or oxyaryleneoxy with 6, 12 or 18 carbon atoms; and n is 1 to 4.

3. A compound according to claim 2 having thé formula:

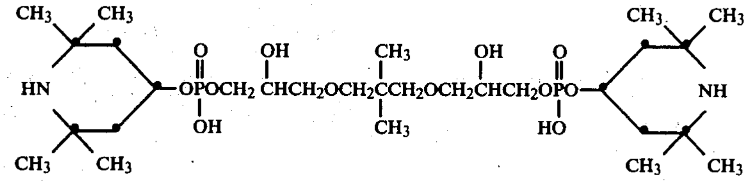

4. A compound according to claim 2 having the formula:

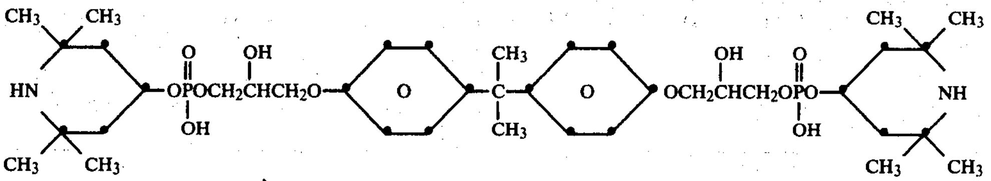

5. A piperidinyl phosphate according to claim 1 having the formula:

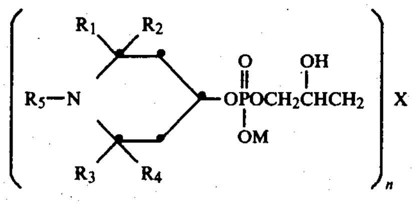

wherein $R_1$ and $R_2$ are each alkyl having 1–6 carbons; $R_3$ and $R_4$ are each alkyl having 1–6 carbons or together with the carbon to which they are bonded form a cyclopentyl or cyclohexyl ring which is unsubstituted or substituted with a methyl group; $R_5$ is hydrogen, oxy, alkyl having 1 to 12 carbon atoms, β-methoxyethyl, alkenyl having 3 or 4 carbon atoms, propargyl, benzyl or alkyl substituted benzyl; M is a metal ion selected from the group consisting of Li, Na, K, Mg, Ca, Ba, Mn, Co, Ni, Sn, Zn, Ce; X is an alkyl alkylene, oxyalkyl or oxyalkyleneoxy having 2 to 12 carbon atoms or an aryl, arylene, oxyaryl or oxyaryleneoxy with 6, 12 or 18 carbon atoms; and n is 1 to 4.

6. A compound according to claim 5 having the formula:

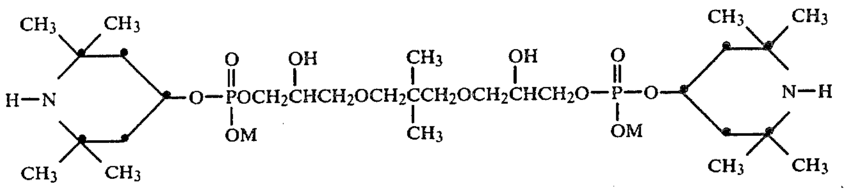

wherein M is a metal ion selected from the group consisting of Li, Na, K, Mg, Ca, Ba, Mn, Co, Ni, Sn, Zn and Ce.

7. A compound according to claim 5 having the formula:

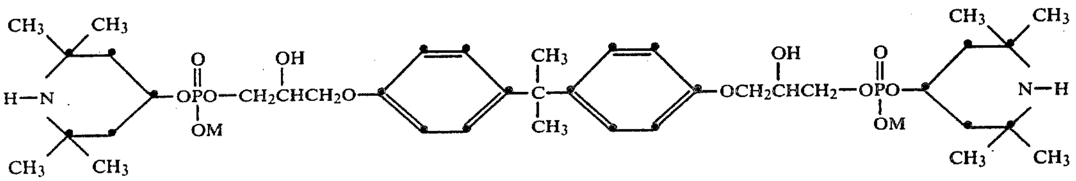

wherein M is a metal ion selected from the group consisting of Li, Na, K, Mg, Ca, Ba, Mn, Co, Ni, Sn, Zn and Ce.

8. A compound according to claim 6 wherein said metal ion is potassium.

9. A compound according to claim 6 wherein said metal ion is nickel.

10. A compound according to claim 6 wherein said metal ion is cerium.

11. A compound according to claim 6 wherein said metal ion is zinc.

12. A compound according to claim 7 wherein said metal ion is zinc.

* * * * *